US006307027B1

(12) United States Patent
Linemeyer et al.

(10) Patent No.: US 6,307,027 B1

(45) Date of Patent: Oct. 23, 2001

(54) BRADYKININ $B_1$ RECEPTOR ANTIBODIES

(75) Inventors: David L. Linemeyer; John W. Hess; Joseph A. Borkowski, all of Westfield; Kathleen K. Bierilo, Matawan; John G. Menke, Morganville, all of NJ (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/307,912

(22) Filed: May 10, 1999

Related U.S. Application Data

(60) Continuation of application No. 08/932,761, filed on Sep. 17, 1997, now Pat. No. 5,965,367, which is a division of application No. 08/229,418, filed on Apr. 15, 1994, now Pat. No. 5,712,111.

(51) Int. Cl.[7] .......................... C07K 16/28

(52) U.S. Cl. .......................... 530/388.22; 530/387.9

(58) Field of Search .......................... 435/69.1, 7.1, 435/7.2, 282.3, 320.1, 501; 530/350, 388.22, 387.8; 536/23.5

(56) References Cited

U.S. PATENT DOCUMENTS

| | | | |
|---|---|---|---|
| 5,712,111 * | 1/1998 | Linemeyer et al. | 435/69.1 |
| 5,965,367 * | 10/1999 | Linemeyer et al. | 435/6 |

OTHER PUBLICATIONS

Menke et al. Expression Cloning of a Human B1 Bradykinin Receptor. J. Biol. Chem. 269(34):21583–21586, Aug. 1994.*

Phillips et al. Expression of Functional Bradykinin Receptors in Xenopus Oocytes. J. Neurochem. 58(1):243–249, 1992.*

Atassi. Preparation of Monoclonal Antibodies to Preselected Protein Regions. Meth. in Enzymol. 121:69–95, 1986.*

Perkins, Martin N. et al., Antinociceptive activity of the bradykinin $B_1$ and $B_2$ receptor antagonists, des–Arg$^9$, [Leu$^8$]—BK and HOE 140, in two models of persistent hyperalgesia in the rat. Pain, vol. 53, p. 191–197, 1993.

McEachern, Adrienne E., et al., Expression cloning of a rat B2 bradykinin receptor, Proc. Natl. Acad. Sci. USA, vol. 88, p. 7724–7728, 1991.

Burch and Axelrod, Dissociation of bradykinin–induced prostaglandin formation from phosphatidylinositol turnover in Swiss 3T3 fibroblast: Evidence for G protein regulation of phospholipase $A_2$ *PNAS* 84: 6374–6378 (1987).

Strader, Catherine et al., Structural basis of B–adrenergic receptor function, The FASEB Journal, vol. 3, p. 1825–1832, 1989.

Chartrain, Nicols et al., Molecular Cloning, Structure, and Chromosomal Localization of the Human Inducible Nitric Oxide Synthase Gene. The Journal of Biological Chemistry, vol. 269, No. 9, p. 6765–6772, 1994.

Rinas, Ursula, et al., Characterization of Recombinant Factor XIlla Produced in *Saccharomyces Cerevisiae*, Biotechnology, p. 543–546, 1990.

Perkins & Kelly, Induction of bradykinin $B_1$ receptors in vivo in a model of ultra–violet irradiation–induced thermal hyperalgesia in the rat, Br. J. Pharmacol., vol. 110, p. 1441–1444, 1993.

Schneck, Kathryn, et al., Bradykinin $B_1$ receptors in rabbit aorta smooth muscle cells in culture, European J. of Pharmacol., vol. 266, p. 277–282, 1994.

Tropea, Margaret et al., $B_1$ and $B_2$ kinin receptors on cultured rabbit superior mesenteric artery smooth muscle cells: receptor–specific stimulation of inositol phosphate formation and arachidonic acid release by des–arg–bradykinin and bradykinin, Journal of Pharmacol and Experimental Therapeutics, vol. 264, No. 2, p. 930–937, 1993.

Horowitz, Burton et al., Synthesis and Assembly of Functional Mammalian Na, K–ATPase in Yeast, Journal of Biological Chemistry, vol. 265, No. 8, p. 4189–4192, 1990.

Goldstein & Wall, Activation of Protein Formation and Cell Division by Bradykinin and Des–Arg$^9$–bradykinin, The Journal of Biological Chemistry, vol. 259, No. 14, p. 9263–9268, 1984.

Slivka and Insel, Phorbol Ester and Neomycin Dissociate Bradykinin Receptor–mediated Arachidonic Acid Release and Polyphosphoinositide Hydrolysis in Madin–Darby Canine Kidney Cells, Journal of Biological Chemistry, vol. 263, No. 29, p. 14640–14647, 1988.

Regoli and Barabe, Pharmacology of Bradykinin and Related Kinins, Pharmacological Reviews, vol. 32, No. 1, p. 1–46, 1980.

Masu, Yasuo et al., cDNA cloning of bovine substance–K receptor through oocyle expression system, Nature, vol. 329, p. 836–838, 1987.

Dray and Perkins, Bradykinin and inflammatory pain, J. Neurophysiol., vol. 63, p. 256–272, 1993.

Couture, R. et al., Peptides and the human colon: an in vitro pharmacological study, Can. J. Physiol. Pharmacol., vol. 59, p. 957–964 1981.

Wirth, Klaus et al., DesArg$^9$–D–Arg[Hyp$^3$, Thi$^5$, D–Tic$^7$, Oic$^8$]bradykinin (desArg$^{10}$–[Hoe140]) is a potent bradykinin $B_1$ receptor antagonist, European Journal of Pharmacology, vol. 205, p. 217–218, 1991.

(List continued on next page.)

*Primary Examiner*—John Ulm

(74) *Attorney, Agent, or Firm*—J. Mark Hand; Jack L. Tribble

(57) ABSTRACT

DNAs encoding bradykinin $B_1$ receptors from mammalian cells have been cloned and characterized. The recombinant receptor is capable of forming receptors which bind desArg$^{10}$ kallidin and other $B_1$-specific ligands. The DNA has been expressed in recombinant host cells which produce active recombinant protein. In addition, the recombinant host cells are utilized to establish a method for identifying modulators of the receptor activity, and receptor modulators are identified.

8 Claims, 5 Drawing Sheets

OTHER PUBLICATIONS

Regoli, Domenico et al., Conversion of kinins and their antagonists into $B_1$ Receptor activators and blockers in isolated vessels, European Journal of Pharmacology, vol. 127, p. 219–224, 1986.

Regoli, D. et al., Receptors for bradykinin in rabbit aortae, Can. J. Physiol. Pharmacol., vol. 55, p. 855–867, 1977.

Regoli, D. et al., De novo formation of vascular receptors for bradykinin[1], Can. J. Physiol. Pharmacol, vol. 56, p. 674–677, 1978.

Regoli, Domenico et al., Induction of $B_1$–Receptors for kinins in the rabbit by a bacterial lipopolysaccharide, European Journal of Pharmacology, vol. 71, p. 105–115, 1981.

Farmer, S.G. et al., Induction of vascular smooth muscle bradykinin $B_1$ receptors in vivo during antigen arthritis, Agents and Actions, vol. 34, p. 191–193, 1991.

Deblois, Denis et al., Effect of glucocorticoids, monokines and growth factors on the spontaneously developing responses of the rabbit isolated aorta to des–$Arg^9$–bradykinin, Br. J. Pharmacol., vol. 93, p. 969–977, 1988.

deBiois, Denis et al., Pulse exposure to protein synthesis inhibitors enhances vascular responses to des–$Arg^9$–bradykinin: possible role of interleukin–1, Br. J. Pharmacol. vol. 103, p. 1057–1066, 1991.

deBlois, Denis et al., Pharmacological modulation of the up–regulated responses to des–$Arg^9$–bradykinin in vivo and in vitro, Immunopharmacology, vol. 17, p. 187–198, 1989.

Burch, R.M. et al., The Kallikrein–kininogen–kinin system in chronic inflammation, Agents and Actions, vol. 27, 3/4, p. 258–260, 1989.

Tiffany and Burch, Bradykinin stimulates tumor necrosis factor and interleukin–1 release from macrophages, vol. 247, No. 2, 189–192, 1989.

Proud, David, Kinin formation: Mechanisms and role in inflammatory disorders, Ann.Rev.Immunol., vol. 6: p. 49–83, 1988.

Rhaleb, N. et al., Receptors for kinins in isolated arterial vessels of dogs, European Journal of Pharmacology, vol. 162, p. 419–427 (1989).

Lortie, Mark et al., The Role of $B_1$–and $B_2$–kinin receptors in the renal tubular and hemodynamic response to bradykinin, American Physiological Society, vol. 262, p. R72–R76, 1992.

Powell, Steven J. et al., Human Bradykinin $B_2$ Receptor: Nucleotide Sequence Analysis and Assignment to Chromosome 14, Genomics, vol. 15, p. 435–438, 1993.

Hess, Fred J. et al., Cloning and Pharmacological Characterization of a Human Bradykinin (BK–2) Receptor, Biochemical and Biophysical Research Communications, vol. 184, No. 1, p. 260–268, 1992.

Eggerickx, Dominique et al., Molecular Cloning, Functional Expression and Pharmacological Characterization of a Human Bradykinin $B_2$ Receptor Gene, vol. 187, No. 3, p. 1306–1313, 1992.

Hock, F.J. et al., Hoe 140 a new potent and long acting bradykinin–anagonist: in vitro studies, J. Pharmacol., vol. 102, p. 769–773, 1991.

Sandberg, Kathryn et al., Calcium mobilization by angiotensin II and nerotransmitter receptors expressed in *Xenopus laevis* oocyles, FEBS Letters, vol. 241, No. 1,2 p. 177–180, 1988.

Huang, Ruey–Ruey C., et al., Identification of Allosteric Antagonists of Receptor–Guanine Nucleotide–Binding Protein Interactions, Molecular Pharmacology, vol. 37, p. 304–310, 1989.

Kitts, Paul A. et al., Linearization of baculovirus DNA enhances the recovery of recombinant virus expression vectors, Nucleic Acids Research, vol. 18, No. 19, 1990.

Hess, Fred J. et al., Differential Pharmacology of Cloned Human and Mouse $B_2$ Bradykinin Receptors, Molecular Pharmacology, vol. 45, p. 1–8, 1993.

McIntyre et al. "Cloned Murine Bradykinin Receptor Exhibits a Mixed $B_1$ and $B_2$ Pharmacological Selectivity", Mol. Pharmacol., vol. 44, pp 346–355 (1992).

Webb et al, '$B_1$ and $B_2$ Bradykinin Receptors . . . mRNAs' J. of Neurochemistry, vol. 62, No. 4 1994 pp1247–1253.

* cited by examiner

CAGAGAAAACTCCTCCAAAAGCAGCTCTCACTATCAGAAAACCCAACTAC
AGTTGTGAACGCCTTCATTTTCTGCCTGAGGTCTCAGTCCGTCGGCCCAG
ACTGAAGTGCAGTGGCACAATCATAGCTCGCTGCAGCCTCGACCTTCCAG
GCTTAAACGATTCTCCCACCTCAGCCTCTCGAGTTGCTGGGACCACAGGT
CACTGTGCATGGCATCATCCTGGCCCCCTCTAGAGCTCCAATCCTCCAAC
CAGAGCCAGCTCTTCCCTCAAAATGCTACGGCCTGTGACAATGCTCCAGA
AGCCTGGGACCTGCTGCACAGAGTGCTGCCGACATTTATCATCTCCATCT
GTTTCTTCGGCCTCCTAGGGAACCTTTTTGTCCTGTTGGTCTTCCTCCTG
CCCCGGCGGCAACTGAACGTGGCAGAAATCTACCTGGCCAACCTGGCAGC
CTCTGATCTGGTGTTTGTCTTGGGCTTGCCCTTCTGGGCAGAGAATATCT
GGAACCAGTTTAACTGGCCTTTCGGAGCCCTCCTCTGCCGTGTCATCAAC
GGGGTCATCAAGGCCAATTTGTTCATCAGCATCTTCCTGGTGGTGGCCAT
CAGCCAGGACCGCTACCGCGTGCTGGTGCACCCTATGGCCAGCGGAAGGC
AGCAGCGGCGGAGGCAGGCCCGGGTCACCTGCGTGCTCATCTGGGTTGTG
GGGGGCCTCTTGAGCATCCCCACATTCCTGCTGCGATCCATCCAAGCCGT
CCCAGATCTGAACATCACCGCCTGCATCCTGCTCCTCCCCCATGAGGCCT
GGCACTTTGCAAGGATTGTGGAGTTAAATATTCTGGGTTTCCTCCTACCA
CTGGCTGCGATCGTCTTCTTCAACTACCACATCCTGGCCTCCCTGCGAAC
GCGGGAGGAGGTCAGCAGGACAAGGTGCGGGGGCCGCAAGGATAGCAAGA
CCACAGCGCTGATCCTCACGCTCGTGGTTGCCTTCCTGGTCTGCTGGGCC
CCTTACCACTTCTTTGCCTTCCTGGAATTCTTATTCCAGGTGCAAGCAGT
CCGAGGCTGCTTTTGGGAGGACTTCATTGACCTGGGCCTGCAATTGGCCA
ACTTCTTTGCCTTCACTAACAGCTCCCTGAATCCAGTAATTTATGTCTTT
GTGGGCCGGCTCTTCAGGACCAAGGTCTGGGAACTTTATAAACAATGCAC
CCCTAAAAGTCTTGCTCCAATATCTTCATCCCATAGGAAAGAAATCTTCC
AACTTTTCTGGCGGAATTAAAACAGCATTGAACCAAGAAAAAAAAAAAAA
AAAAAAA SEQ. ID.NO.:1

FIG.1

Met Ala Ser Ser Trp Pro Pro Leu Glu Leu Gln Ser Ser Asn Gln
Ser Gln Leu Phe Pro Gln Asn Ala Thr Ala Cys Asp Asn Ala Pro
Glu Ala Trp Asp Leu Leu His Arg Val Leu Pro Thr Phe Ile Ile
Ser Ile Cys Phe Phe Gly Leu Leu Gly Asn Leu Phe Val Leu Leu
Val Phe Leu Leu Pro Arg Arg Gln Leu Asn Val Ala Glu Ile Tyr
Leu Ala Asn Leu Ala Ala Ser Asp Leu Val Phe Val Leu Gly Leu
Pro Phe Trp Ala Glu Asn Ile Trp Asn Gln Phe Asn Trp Pro Phe
Gly Ala Leu Leu Cys Arg Val Ile Asn Gly Val Ile Lys Ala Asn
Leu Phe Ile Ser Ile Phe Leu Val Val Ala Ile Ser Gln Asp Arg
Tyr Arg Val Leu Val His Pro Met Ala Ser Gly Arg Gln Gln Arg
Arg Arg Gln Ala Arg Val Thr Cys Val Leu Ile Trp Val Val Gly
Gly Leu Leu Ser Ile Pro Thr Phe Leu Leu Arg Ser Ile Gln Ala
Val Pro Asp Leu Asn Ile Thr Ala Cys Ile Leu Leu Leu Pro His
Glu Ala Trp His Phe Ala Arg Ile Val Glu Leu Asn Ile Leu Gly
Phe Leu Leu Pro Leu Ala Ala Ile Val Phe Phe Asn Tyr His Ile
Leu Ala Ser Leu Arg Thr Arg Glu Glu Val Ser Arg Thr Arg Cys
Gly Gly Arg Lys Asp Ser Lys Thr Thr Ala Leu Ile Leu Thr Leu
Val Val Ala Phe Leu Val Cys Trp Ala Pro Tyr His Phe Phe Ala
Phe Leu Glu Phe Leu Phe Gln Val Gln Ala Val Arg Gly Cys Phe
Trp Glu Asp Phe Ile Asp Leu Gly Leu Gln Leu Ala Asn Phe Phe
Ala Phe Thr Asn Ser Ser Leu Asn Pro Val Ile Tyr Val Phe Val
Gly Arg Leu Phe Arg Thr Lys Val Trp Glu Leu Tyr Lys Gln Cys
Thr Pro Lys Ser Leu Ala Pro Ile Ser Ser Ser His Arg Lys Glu
Ile Phe Gln Leu Phe Trp Arg Asn SEQ. ID. NO.:2.

FIG.2

SEQUENCE LISTING

```
(1) GENERAL INFORMATION:

   (iii) NUMBER OF SEQUENCES: 2


(2) INFORMATION FOR SEQ ID NO: 1:

     (i) SEQUENCE CHARACTERISTICS:
          (A) LENGTH: 1307 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO: 1:
```

-continued

```
CAGAGAAAAC TCCTCCAAAA GCAGCTCTCA CTATCAGAAA ACCCAACTAC AGTTGTGAAC     60
GCCTTCATTT TCTGCCTGAG GTCTCAGTCC GTCGGCCCAG ACTGAAGTGC AGTGGCACAA    120
TCATAGCTCG CTGCAGCCTC GACCTTCCAG GCTTAAACGA TTCTCCCACC TCAGCCTCTC    180
GAGTTGCTGG GACCACAGGT CACTGTGCAT GGCATCATCC TGGCCCCCTC TAGAGCTCCA    240
ATCCTCCAAC CAGAGCCAGC TCTTCCCTCA AAATGCTACG GCCTGTGACA ATGCTCCAGA    300
AGCCTGGGAC CTGCTGCACA GAGTGCTGCC GACATTTATC ATCTCCATCT GTTTCTTCGG    360
CCTCCTAGGG AACCTTTTTG TCCTGTTGGT CTTCCTCCTG CCCCGGCGGC AACTGAACGT    420
GGCAGAAATC TACCTGGCCA ACCTGGCAGC CTCTGATCTG GTGTTTGTCT TGGGCTTGCC    480
CTTCTGGGCA GAGAATATCT GGAACCAGTT TAACTGGCCT TTCGGAGCCC TCCTCTGCCG    540
TGTCATCAAC GGGGTCATCA AGGCCAATTT GTTCATCAGC ATCTTCCTGG TGGTGGCCAT    600
CAGCCAGGAC CGCTACCGCG TGCTGGTGCA CCCTATGGCC AGCGGAAGGC AGCAGCGGCG    660
GAGGCAGGCC CGGGTCACCT GCGTGCTCAT CTGGGTTGTG GGGGGCCTCT TGAGCATCCC    720
CACATTCCTG CTGCGATCCA TCCAAGCCGT CCCAGATCTG AACATCACCG CCTGCATCCT    780
GCTCCTCCCC CATGAGGCCT GGCACTTTGC AAGGATTGTG GAGTTAAATA TTCTGGGTTT    840
CCTCCTACCA CTGGCTGCGA TCGTCTTCTT CAACTACCAC ATCCTGGCCT CCCTGCGAAC    900
GCGGGAGGAG GTCAGCAGGA CAAGGTGCGG GGGCCGCAAG GATAGCAAGA CCACAGCGCT    960
GATCCTCACG CTCGTGGTTG CCTTCCTGGT CTGCTGGGCC CCTTACCACT TCTTTGCCTT   1020
CCTGGAATTC TTATTCCAGG TGCAAGCAGT CCGAGGCTGC TTTTGGGAGG ACTTCATTGA   1080
CCTGGGCCTG CAATTGGCCA ACTTCTTTGC CTTCACTAAC AGCTCCCTGA ATCCAGTAAT   1140
TTATGTCTTT GTGGGCCGGC TCTTCAGGAC CAAGGTCTGG GAACTTTATA AACAATGCAC   1200
CCCTAAAAGT CTTGCTCCAA TATCTTCATC CCATAGGAAA GAAATCTTCC AACTTTTCTG   1260
GCGGAATTAA AACAGCATTG AACCAAGAAA AAAAAAAAAA AAAAAAA                 1307
```

(2) INFORMATION FOR SEQ ID NO: 2:

(i) SEQUENCE CHARACTERISTICS:
(A) LENGTH: 353 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 2:

```
Met Ala Ser Ser Trp Pro Pro Leu Glu Leu Gln Ser Ser Asn Gln Ser
1               5                   10                  15

Gln Leu Phe Pro Gln Asn Ala Thr Ala Cys Asp Asn Ala Pro Glu Ala
            20                  25                  30

Trp Asp Leu Leu His Arg Val Leu Pro Thr Phe Ile Ile Ser Ile Cys
        35                  40                  45

Phe Phe Gly Leu Leu Gly Asn Leu Phe Val Leu Leu Val Phe Leu Leu
    50                  55                  60

Pro Arg Arg Gln Leu Asn Val Ala Glu Ile Tyr Leu Ala Asn Leu Ala
65                  70                  75                  80

Ala Ser Asp Leu Val Phe Val Leu Gly Leu Pro Phe Trp Ala Glu Asn
                85                  90                  95

Ile Trp Asn Gln Phe Asn Trp Pro Phe Gly Ala Leu Leu Cys Arg Val
            100                 105                 110
```

-continued

```
Ile Asn Gly Val Ile Lys Ala Asn Leu Phe Ile Ser Ile Phe Leu Val
        115                 120                 125

Val Ala Ile Ser Gln Asp Arg Tyr Arg Val Leu Val His Pro Met Ala
    130                 135                 140

Ser Gly Arg Gln Gln Arg Arg Arg Gln Ala Arg Val Thr Cys Val Leu
145                 150                 155                 160

Ile Trp Val Val Gly Gly Leu Leu Ser Ile Pro Thr Phe Leu Leu Arg
                165                 170                 175

Ser Ile Gln Ala Val Pro Asp Leu Asn Ile Thr Ala Cys Ile Leu Leu
            180                 185                 190

Leu Pro His Glu Ala Trp His Phe Ala Arg Ile Val Glu Leu Asn Ile
        195                 200                 205

Leu Gly Phe Leu Leu Pro Leu Ala Ala Ile Val Phe Phe Asn Tyr His
    210                 215                 220

Ile Leu Ala Ser Leu Arg Thr Arg Glu Glu Val Ser Arg Thr Arg Cys
225                 230                 235                 240

Gly Gly Arg Lys Asp Ser Lys Thr Thr Ala Leu Ile Leu Thr Leu Val
                245                 250                 255

Val Ala Phe Leu Val Cys Trp Ala Pro Tyr His Phe Phe Ala Phe Leu
            260                 265                 270

Glu Phe Leu Phe Gln Val Gln Ala Val Arg Gly Cys Phe Trp Glu Asp
        275                 280                 285

Phe Ile Asp Leu Gly Leu Gln Leu Ala Asn Phe Phe Ala Phe Thr Asn
    290                 295                 300

Ser Ser Leu Asn Pro Val Ile Tyr Val Phe Val Gly Arg Leu Phe Arg
305                 310                 315                 320

Thr Lys Val Trp Glu Leu Tyr Lys Gln Cys Thr Pro Lys Ser Leu Ala
                325                 330                 335

Pro Ile Ser Ser Ser His Arg Lys Glu Ile Phe Gln Leu Phe Trp Arg
            340                 345                 350

Asn
```

BRADYKININ $B_1$ RECEPTOR ANTIBODIES

This application is a continuation application of U.S. application Ser. No. 08/932,761, filed Sep. 17, 1997, now U.S. Pat. No. 5,965,367, which is a divisional application of U.S. application Ser. No. 08/229,418, filed Apr. 15, 1994, now U.S. Pat. No. 5,712,111.

BACKGROUND OF THE INVENTION

Two mammalian bradykinin receptor subtypes, $B_1$ and $B_2$, have been defined based on their pharmacological properties (A. Dray, M. Perkins, *TINS* 16, 99–104 (1993), D. Proud, A. P. Kaplan, *Annual Review Immunology* 6, 49–83 (1988)). The nonapeptide bradykinin (BK) and the decapeptide Lys-BK (kallidin) are liberated from the large protein precursor kininogen by the proteolytic action of kallikreins. Because of their rapid degradation, these peptide hormones are presumed to mediate local effects. BK and kallidin both activate the $B_2$ receptor. These $B_2$ receptor agonists are then degraded by a carboxypeptidase to produce the $B_1$ receptor agonists des-$Arg^9$BK and des-$Arg^{10}$kallidin or by the angiotensin converting enzyme (ACE) to yield inactive peptides. The phenomenon of the proteolytic transformation of a compound from $B_2$ to $B_1$ selectivity has been observed not only for the endogenous kinin agonists but also for several synthetic peptide antagonists (K. Wirth, et al., *European Journal of Pharmacology* 205, 217–218 (1991), D. Regoli, et al., *European Journal of Pharmacology* 127, 219–224 (1986)). BK and kallidin act as equipotent agonists at the $B_2$ bradykinin receptor subtype. In contrast, BK is totally inactive at the $B_1$ bradykinin receptor subtype. Although traditionally des-$Arg^9$BK has been utilized to study the $B_1$ receptor, the most potent agonist for the $B_1$ receptor appears to be des-$Arg^{10}$kallidin (D. Regoli, et al., *European Journal of Pharmacology* 127, 219–224 (1986)).

Bradykinin and kallidin, acting through the $B_2$ receptor present in smooth muscle and certain neurons, cause pronounced hypotension and are potent mediators of pain and inflammation (A. Dray, supra; D. Proud, supra). In contrast, the $B_1$ receptor is not detected in most normal tissues and appears to act predominantly in pathophysiological conditions (A. Dray, supra). The $B_1$ receptor was originally discovered through a contractile response to des-$Arg^9$BK that was observed in rabbit aortic strips only after a prolonged ex vivo incubation (D. Regoli, J. Barabe, W. K. Park, *Canadian Journal of Physiology and Pharmacology* 55, 855–867 (1977); D. Regoli, F. Marceau, J. Barabe, *Canadian Journal of Physiology and Pharmacology* 56, 674–677 (1978); D. Regoli, J. Barabe, Pharmacological Reviews 32, 1–46 (1980)). The de novo synthesis of $B_1$ receptors has been reported in vivo following treatment with bacterial lipopolysaccharide (LPS) (D. C. Regoli, R. Marceau, J. Lavigne, *European Journal of Pharmacology* 71, 105–115 (1981)), and in animal models of antigen arthritis (S. G. Farmer, B. A. McMillan, S. N. Meeker, R. M. Burch, *Agents and Action* 34, 191–193 (1991)). In vitro studies have implicated a number of cytokines, most notably interleukin-1 (IL-1) and IL-2, as mediators that induce the expression of $B_1$ receptors (D. Regoli, supra; D. Deblois, J. Bouthillier, F. Marceau, *British Journal of Pharmacology* 93, 969–977 (1988); D. deBlois, J. Bouthillier, F. Marceau, *British Journal of Pharmacology* 103, 1057–1066 (1991); D. deBlois, J. Bouthillier, R. Marceau, *Immunopharmacology* 17, 187–198 (1989)). These results, in conjunction with the finding that activation of a $B_1$ bradykinin receptor on mouse macrophages causes the release of cytokines (R. M. Burch, J. R. Connor, C. W. Tiffany, *Agents and Action* 27, 258–260 (1989); C. W. Tiffany, R. M. Burch, *FEBS letters* 247, 189–192 (1989)), suggest that the $B_1$ receptor could be an important mediator of chronic inflammation. Significantly, the $B_1$ bradykinin receptor antagonist des-$Arg^9$[$Leu^8$]BK was recently found to alleviate hyperalgesia in animal models of persistent inflammation (A. Dray, supra; M. N. Perkins, D. Kelly, *British Journal of Pharmacology* 110, 1441–1444 (1993); M. N. Perkins, E. Campbell, A. Dray, *Pain* 53, 191–197 (1993)). Thus, a body of evidence implicates the $B_1$ bradykinin receptor in the pathophysiology of inflammation. Relatively little is known about the role for the $B_1$ receptor in healthy tissues, although both $B_1$ and $B_2$ receptors may play a physiological role in renal function (N.-E. Rhaleb, et al., *European Journal of Pharmacology* 162, 419–427 (1989); M. Lortie, D. Regoli, N.-E. Rhaleb, G. E. Plante, *American Journal of Physiology* 262, R72-R76 (1992)). The apparent inducibility of the $B_1$ receptor under pathological conditions may provide a therapeutic window for the use of $B_1$ receptor antagonists in treating chronic inflammation.

The cloning of the $B_2$ bradykinin receptor revealed that this receptor is a member of the superfamily of G-protein coupled receptors (A. E. McEachem, et al., *Proc. Natl. Acad. Sci.* 88, 7724–7728 (1991); S. J. Powell, et al., *Genomics* 15, 435–438 (1993); J. F. Hess, J. A. Borkowski, G. S. Young, C. D. Strader, R. W. Ransom, *Biochem. and Biophys. Res. Comm.* 184, 260–268 (1992); D. Eggerickx, E. Raspe, D. Bertrand, G. Vassart, M. Parmentier, *Biochem. Biophys. Res. Comm.* 187, 1306–1313 (1992)). The rat $B_2$ bradykinin receptor was cloned using a Xenopus oocyte expression system (A. E. McEachem, et al., supra) that exploited the ability of the $B_2$ receptor to act through G-proteins to activate phospholipase C and mobilize $Ca^{2+}$ (R. M. Burch, J. Axelrod, *Proc. Natl. Acad. Sci.* 84, 6374–6378 (1987); S. R. Slivka, P. A. Insel, *J. Biol. Chem* 263, 14640–14647 (1988)). Recently, the $B_1$ bradykinin receptor in rabbit aorta and rat mesangial cultured cells has also been shown to activate phospholipase C leading to $Ca^{2+}$ mobilization (K. A. Schneck, supra; M. Issandou, J.-M. Darbon, *Journal of Biological Chemistry* 259, 9263–9268 (1991); M. M. Tropea, D. Gummelt, M. S. Herzig, L. M. F. Leeb-Lundberg, *Journal of Pharmacology and Experimental Therapeutics* 264, 930–937 (1993)). Furthermore, both $B_1$ and $B_2$ bradykinin receptor activities were detected when mRNA from the human fibroblast cell line WI-38 was injected into *Xenopus laevis* oocytes (E. Phillips, M. J. Conder, S. Bevan, P. McIntyre, M. Webb, *Journal of Neurochemistry* 58, 243–249 (1992). The similarity of ligands for the two bradykinin receptor subtypes suggests a similarity between the $B_1$ and $B_2$ receptor genes. However, the results of genomic Southern analyses indicated that these two receptors are not highly homologous (A. E. McEachern, et al., supra; J. F. Hess, et al., *Molecular Pharmacology* 45, 1–8 (1994). Therefore, in order to clone the human $B_1$ receptor, we pursued an expression cloning strategy in Xenopus oocytes utilizing the photoprotein aequorin as an indicator of $Ca^{2+}$ mobilization (K. Sandberg, A. J. Markwick, D. P. Trinh, K. J. Catt, *FEBS Letters* 241, 177–180 (1988); E. Giladi, E. R. Spindel, *BioTechniques* 10, 744–747 (1991). We isolated a cDNA clone that encodes a G-protein coupled receptor with an amino acid sequence that is 36% identical to that of the $B_2$ bradykinin receptor. The pharmacological properties of this cloned receptor expressed in mammalian cells demonstrate that it is a $B_1$ bradykinin receptor.

SUMMARY OF THE INVENTION

The bradykinin $B_1$ receptor has been cloned, expressed and characterized. Using a recombinant expression system functional DNA clones encoding the receptor have been isolated. The pharmacological and structural properties of the protein are disclosed, as are the amino acid and nucleotide sequences. The recombinant protein is useful to identify modulators of the receptor. Modulators identified in this process are useful as therapeutic agents. Modulators, as described herein, include but are not limited to agonists, antagonists, suppressors and inducers.

BRIEF DESCRIPTION OF THE DRAWINGS

FIG. 1—The DNA sequence of the human bradykinin receptor $B_1$ is shown SEQ ID no:1.

FIG. 2—The amino acid sequence of the human bradykinin receptor $B_1$ is shown SEQ ID no:2.

DETAILED DESCRIPTION

Figure 3:
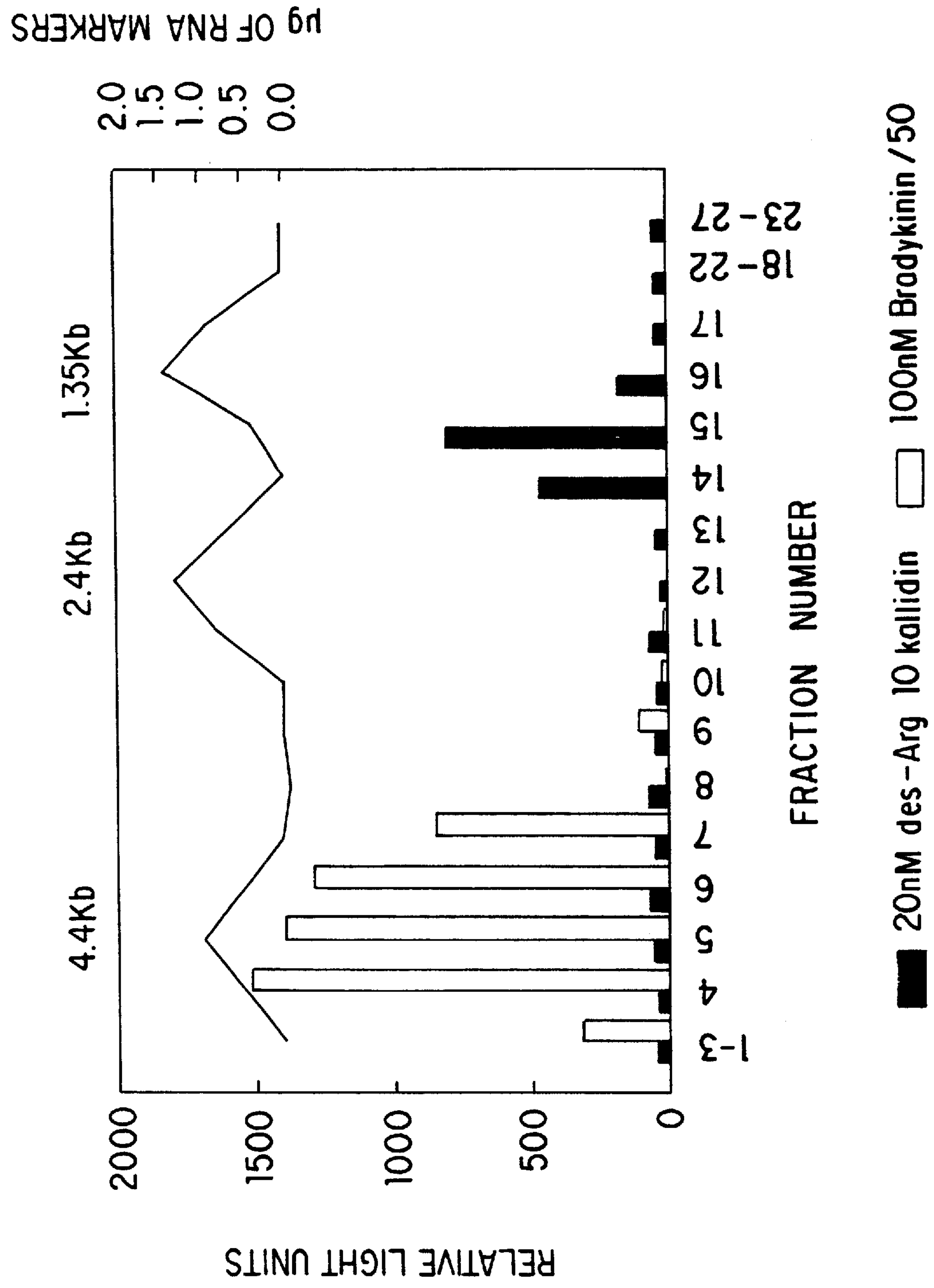
FIG. 3—Relative light units are presented in response to 100 nM bradykinin (open bars) and 20 nM des-$Arg^{10}$kallidin (closed bars) with increasing fraction number (decreasing in size). Oocytes were injected with an equal volume of sucrose-gradient size fractionated IL-1β induced IMR-90 poly$(A)^+$ mRNA and challenged with bradykinin agonists. The relative light units obtained with 100 nM bradykinin were divided by 50 to allow plotting both data sets on the same graph. A trace indicating the RNA size markers that were fractionated in a parallel gradient is shown in the upper portion of the figure.

The present invention relates to DNA encoding a bradykinin $B_1$ receptor ($B_1$) which is isolated from $B_1$ producing cells. $B_1$, as used herein, refers to protein which can specifically function as the $B_1$ bradykinin receptor subtype.

The amino acid and DNA sequences of $B_1$ were not previously known. Cells capable of producing $B_1$ include, but are not limited to, aortic smooth muscle cells. Cell lines which may produce $B_1$ include, but are not limited to, IMR-90 and WI-38. The preferred cells for the present invention are IMR-90 cells.

Other cells and cell lines may also be suitable for use to isolate $B_1$ cDNA. Selection of suitable cells may be done by screening for $B_1$ activity in whole cells or cell extracts. Methods for detecting $B_1$ activity are known in the art and either measure the ability to bind ligands known to interact at the $B_1$ receptor subtype, such as des-$Arg^{10}$kallidin, des-$Arg^9$bradykinin, des-$Arg^{10}Leu^9$kallidin, and des-$Arg^9Leu^8$bradykinin, or measure phosphatidyl inositol hydrolysis, release of intracellular $Ca^{2+}$ stores, or arachidonic acid release mediated by des-$Arg^{10}$kallidin or des-$Arg^9$bradykinin. Cells which possess $B_1$ activity in such assays may be suitable for the isolation of $B_1$ DNA.

Because the genetic code is degenerate, more than one codon may be used to encode a particular amino acid, and therefore, the amino acid sequence can be encoded by any of a set of similar DNA oligonucleotides. Only one member of the set will be identical to the $B_1$ sequence but will be capable of hybridizing to $B_1$ DNA even in the presence of DNA oligonucleotides with mismatches under appropriate conditions. Under alternate conditions, the mismatched DNA oligonucleotides may still hybridize to the $B_1$ DNA to permit identification and isolation of $B_1$ encoding DNA.

DNA encoding $B_1$ from a particular organism may be used to isolate and purify homologues of $B_1$ from other organisms. To accomplish this, the first $B_1$ DNA may be mixed with a sample containing DNA encoding homologues of $B_1$ under appropriate hybridization conditions. The hybridized DNA complex may be isolated and the DNA encoding the homologous DNA may be purified therefrom.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate or a receptor for a ligand.

As used herein, a "functional derivative" of $B_1$ is a compound that possesses a biological activity (either functional or structural) that is substantially similar to the biological activity of $B_1$. The term "functional derivatives" is intended to include the "fragments," "variants," "degenerate variants," "analogs" and "homologues" or to "chemical derivatives" of $B_1$. The term "fragment" is meant to refer to any polypeptide subset of $B_1$. The term "variant" is meant to refer to a molecule substantially similar in structure and function to either the entire $B_1$ molecule or to a fragment thereof. A molecule is "substantially similar" to $B_1$ if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical.

The term "analog" refers to a molecule substantially similar in function to either the entire B1 molecule or to a fragment thereof.

Any of a variety of procedures known in the art may be used to molecularly clone $B_1$ DNA. These methods include, but are not limited to, direct functional expression of the $B_1$ genes following the construction of a $B_1$-containing cDNA or genomic DNA library in an appropriate expression vector system. Another method is to screen $B_1$-containing cDNA or genomic DNA library constructed in a bacteriophage or plasmid shuttle vector with a labeled oligonucleotide probe designed from the amino acid sequence of the $B_1$ subunits. An additional method consists of screening a $B_1$-containing cDNA or genomic DNA library constructed in a bacteriophage or plasmid shuttle vector with a partial DNA encoding the $B_1$ receptor. This partial DNA is obtained by the specific PCR amplification of $B_1$ DNA fragments through the design of degenerate oligonucleotide primers from the amino acid sequence of the purified $B_1$ receptor. Another method is to isolate RNA from $B_1$-producing cells and translate the RNA into protein via an in vitro or an in vivo translation system. The translation of the RNA into a peptide or a protein will result in the production of at least a portion of the $B_1$ protein which can be identified by, for example, by the activity of $B_1$ receptor protein or by immunological reactivity with an anti-$B_1$ antibody. In this method, pools of RNA isolated from $B_1$-producing cells can be analyzed for the presence of an RNA which encodes at least a portion of the $B_1$ protein. Further fractionation of the RNA pool can be done to purify the $B_1$ RNA from non-$B_1$ RNA. The peptide or protein produced by this method may be analyzed to provide amino acid sequences which in turn are used to provide primers for production of $B_1$ cDNA, or the RNA used for translation can be analyzed to provide nucleotide sequences encoding $B_1$ and produce probes for the production of $B_1$ cDNA. These methods are known in the art and can be found in, for example, Sambrook, J., Fritsch, E. F., Maniatis, T. in Molecular Cloning: A Laboratory Manual, Second Edition, Cold Spring Harbor Laboratory Press, Cold Spring Harbor, N.Y. 1989.

It is readily apparent to those skilled in the art that other types of libraries, as well as libraries constructed from other cells or cell types, may be useful for isolating $B_1$-encoding DNA. Other types of libraries include, but are not limited to, cDNA libraries derived from other cells or cell lines other than IMR-90 cells, and genomic DNA libraries.

It is readily apparent to those skilled in the art that suitable cDNA libraries may be prepared from cells or cell lines which have $B_1$ activity. The selection of cells or cell lines for use in preparing a cDNA library to isolate $B_1$ cDNA may be done by first measuring cell associated $B_1$ activity using the ligand binding assay described fully herein.

Preparation of cDNA libraries can be performed by standard techniques well known in the art. Well known cDNA library construction techniques can be found for example, Sambrook, J., Fritsch, E. F., Maniatis, T. in Molecular Cloning: A Laboratory Manual, Second Edition (Cold Spring Harbor Laboratory, Cold Spring Harbor, N.Y., 1989).

It is also readily apparent to those skilled in the art that DNA encoding B1 may also be isolated from a suitable genomic DNA library. Construction of genomic DNA libraries can be performed by standard techniques well known in the art. Well known genomic DNA library construction techniques can be found in Sambrook, J., Fritsch, E. F., Maniatis, T. in Molecular Cloning: A Laboratory Manual, Second Edition (Cold Spring Harbor Laboratory, Cold Spring Harbor, N.Y., 1989).

In order to clone the $B_1$ gene by the above methods, the amino acid sequence of $B_1$ may be necessary. To accomplish this, $B_1$ protein may be purified and partial amino acid sequence determined by manual sequencing or automated sequenators. It is not necessary to determine the entire amino acid sequence, but the linear sequence of two regions of 6 to 8 amino acids from the protein is determined for the production of primers for PCR amplification of a partial $B_1$ DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the $B_1$ sequence but will be capable of hybridizing to $B_1$ DNA even in the presence of DNA oligonucleotides with mismatches under appropriate conditions. Under alternate conditions, the mismatched DNA oligonucleotides may still sufficiently hybridize to the $B_1$ DNA to permit identification and isolation of $B_1$ encoding DNA.

Purified biologically active $B_1$ may have several different physical forms. $B_1$ may exist as a full-length nascent or unprocessed polypeptide, or as partially processed polypeptides or combinations of processed polypeptides. The full-length nascent $B_1$ polypeptide may be postranslationally modified by specific proteolytic cleavage events which result in the formation of fragments of the full length nascent polypeptide. A fragment, or physical association of fragments may have the full biological activity associated with $B_1$ (specific binding of des-$Arg^{10}$kallidin, and des-$Arg^9$bradykinin) however, the degree of $B_1$ activity may vary between individual $B_1$ fragments and physically associated $B_1$ polypeptide fragments.

$B_1$ in substantially pure form derived from natural sources or from recombinant host cells according to the purification processes described herein, is found to be a polypeptide encoded by a single MRNA. The $B_1$ polypeptide was found to have an apparent molecular weight of about 40.4 kDa.

The cloned $B_1$ DNA obtained through the methods described herein may be recombinantly expressed by molecular cloning into an expression vector containing a suitable promoter and other appropriate transcription regulatory elements, and transferred into prokaryotic or eukaryotic host cells to produce recombinant $B_1$. Techniques for such manipulations are fully described in Sambrook, J., et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells, fungal cells and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant $B_1$ in mammalian cells. Commercially available mammalian expression vectors which may be suitable for recombinant $B_1$ expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express recombinant $B_1$ in bacterial cells. Commercially available bacterial expression vectors which may be suitable for recombinant $B_1$ expression include, but are not limited to pET11a (Novagen), lambda gt11 (Invitrogen), pcDNAII (Invitrogen), pKK223-3 (Pharmacia).

A variety of fungal cell expression vectors may be used to express recombinant $B_1$ in fungal cells. Commercially available fungal cell expression vectors which may be suitable for recombinant $B_1$ expression include but are not limited to pYES2 (Invitrogen), Pichia expression vector (Invitrogen).

A variety of insect cell expression vectors may be used to express recombinant $B_1$ in insect cells. Commercially available insect cell expression vectors which may be suitable for recombinant expression of $B_1$ include but are not limited to pBlue Bac III (Invitrogen).

An expression vector containing DNA encoding $B_1$ may be used for expression of $B_1$ in a recombinant host cell. Recombinant host cells may be prokaryotic or eukaryotic, including but not limited to bacteria such as *E. coli*, fungal cells such as yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M($TK^-$) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, lipofection, protoplast fusion, and electroporation. The expression vector-containing cells are clonally propagated and individually analyzed to determine whether they produce $B_1$ protein. Identification of $B_1$ expressing host cell clones may be done by several means, including but not limited to immunological reactivity with anti-$B_1$ antibodies, and the presence of host cell-associated $B_1$ activity, such as $B_1$-specific ligand binding or signal transduction defined as a response mediated by the interaction of $B_1$-specific ligands at the receptor.

Expression of $B_1$ DNA may also be performed using in vitro produced synthetic mRNA or native mRNA. Synthetic mRNA or mRNA isolated from $B_1$ producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the $B_1$ DNA sequence(s) that yields optimal levels of $B_1$ activity and/or $B_1$ protein, $B_1$ DNA molecules including, but not limited to, the following can be constructed: the full-length open reading frame of the $B_1$ DNA (encoding a protein of about 40.4 kDa=about base 209 to about base 1267) and several constructs containing portions of the DNA encoding $B_1$ protein. All constructs can be designed to contain none, all or portions of the 5' or the 3' untranslated region of $B_1$ DNA. $B_1$ activity and levels of protein expression can be determined following the introduction, both singly and in combination, of these constructs into appropriate host cells. Following determination of the $B_1$ DNA cassette yielding optimal expression in transient assays, this $B_1$ DNA construct is transferred to a variety of expression vectors, for expression in host cells including, but not limited to, mammalian cells, insect cells, *E. coli*, and yeast cells such as *S. cerevisiae*.

Host cell transfectants and microinjected oocytes may be assayed for both the levels of $B_1$ receptor activity and levels of $B_1$ protein by the following methods. One method for assessing $B_1$ receptor activity involves the direct measurement of binding of specific ligands. In the case of recombinant host cells, this involves the transfection or co-transfection of plasmids containing the $B_1$ DNA. In the case of oocytes, this involves the injection of synthetic or native RNAs for $B_1$. Following an appropriate period of time to allow for expression, $B_1$ activity is measured. One method for detecting $B_1$ activity involves the direct measurement of $B_1$ activity in whole cells or cellular lysates prepared from host cells transfected with $B_1$ DNA or oocytes injected with $B_1$ RNA. $B_1$ activity is measured by the specific ligand binding characteristics of the $B_1$ receptor or the response to calcium mobilization or phosphatidyl inositol hydrolysis mediated by $B_1$-specific modulators in host cells expressing $B_1$ DNA or RNA. Modulators, as described herein, include but are not limited to agonists, antagonists, suppressors and inducers.

Following expression of $B_1$ in a recombinant host cell, $B_1$ protein may be recovered to provide $B_1$ in purified form. Several $B_1$ purification procedures are available and suitable for use. As described herein, recombinant $B_1$ may be purified from cell lysates and extracts by various combinations of, or individual application of salt fractionation, ion exchange chromatography, size exclusion chromatography, hydroxylapatite adsorption chromatography and hydrophobic interaction chromatography.

In addition, recombinant $B_1$ can be separated from other cellular proteins by use of an immunoaffinity column made with monoclonal or polyclonal antibodies specific for full length nascent $B_1$, or polypeptide fragments of $B_1$.

Monospecific antibodies to $B_1$ are purified from mammalian antisera containing antibodies reactive against $B_1$ or are prepared as monoclonal antibodies reactive with B1 using the technique of Kohler and Milstein, *Nature* 256, 495–497 (1975). Monospecific antibody as used herein is defined as a single antibody species or multiple antibody species with homogenous binding characteristics for $B_1$. Homogenous binding as used herein refers to the ability of the antibody species to bind to a specific antigen or epitope, such as those associated with the $B_1$, as described above. $B_1$ specific antibodies are raised by immunizing animals such as mice, rats, guinea pigs, rabbits, goats, horses and the like, with rabbits being preferred, with an appropriate concentration of $B_1$ either with or without an immune adjuvant.

Preimmune serum is collected prior to the first immunization. Each animal receives between about 0.1 $\mu$g and about 1000 $\mu$g of $B_1$ associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of $B_1$ in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with $B_1$ are prepared by immunizing inbred mice, preferably Balb/c, with $B_1$. The mice are immunized by the IP or SC route with about 0.1 μg to about 10 μg, preferably about 1 μg, of $B_1$ in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 μg of $B_1$ in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 molecular weight, at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using $B_1$ as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in *Tissue Culture Methods and Applications*, Kruse and Paterson, Eds., Academic Press, 1973.

Monoclonal antibodies are produced in vivo by injection of pristane primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti- $B_1$ mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of $B_1$ in body fluids or tissue and cell extracts.

It is readily apparent to those skilled in the art that the above described methods for producing monospecific antibodies may be utilized to produce antibodies specific for $B_1$ polypeptide fragments, or full-length nascent $B_1$ polypeptide. Specifically, it is readily apparent to those skilled in the art that monospecific antibodies may be generated which are specific for the fully functional receptor or fragments thereof.

$B_1$ antibody affinity columns are made by adding the antibodies to Affigel-10 (Biorad), a gel support which is activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HC1 (pH 8). The column is washed with water followed by 0.23 M glycine HC1 (pH 2.6) to remove any non-conjugated antibody or extraneous protein. The column is then equilibrated in phosphate buffered saline (pH 7.3) and the cell culture supernatants or cell extracts containing $B_1$ are slowly passed through the column. The column is then washed with phosphate buffered saline until the optical density (A280) falls to background, then the protein is eluted with 0.23 M glycine-HCI (pH 2.6). The purified $B_1$ protein is then dialyzed against phosphate buffered saline.

The human embryonic fibroblast cell line IMR-90 had been shown previously to express the $B_1$ bradykinin receptor subtype (R. H. Goldstein, M. Wall, *Journal of Biological Chemistry* 259, 9263–9268 (1984). A more detailed pharmacological characterization revealed the presence of approximately 5000 high affinity binding sites for the $B_1$ agonist $[^3H]$des-$Arg^{10}$kallidin and approximately 70,000 high affinity binding sites for the $B_2$ agonist $[^3H]$bradykinin per cell. The ability of the $B_1$ receptor expressed in IMR-90 cells to mobilize $Ca^{2+}$ in response to des-$Arg^{10}$kallidin was demonstrated using FURA-2 as an indicator. Furthermore, treatment of IMR-90 cells with the cytokine IL-1β was found to stimulate the number of $B_1$ bradykinin receptors approximately 7-fold. Based on these data IL-1β induced IMR-90 cells were used as the source of mRNA for expression cloning.

A cDNA clone encoding a human $B_1$ bradykinin receptor was isolated from an IMR-90 fibroblast cDNA library by expression cloning. The photoprotein aequorin was utilized as an indicator of the ability of the $B_1$ receptor agonist des-$Arg^{10}$kallidin to mediate $Ca^2$+ mobilization in *Xenopus laevis* oocytes injected with IMR-90 derived RNA. A single clone was isolated with an approximately 1307 bp insert which contains an open reading frame encoding an approximately 353 amino acid protein with the characteristics of a G-protein coupled receptor. The amino acid sequence of the $B_1$ bradykinin receptor is about 36% identical to the amino acid sequence of the $B_2$ bradykinin receptor. The $B_1$ bradykinin receptor expressed in COS-7 cells exhibits high affinity binding for $[^3H]$des-$Arg^{10}$kallidin and low affinity for bradykinin. The $B_1$ receptor antagonist des-$Arg^{10}[Leu^9]$ kallidin effectively displaces $[^3H]$des-$Arg^{10}$kallidin from the cloned receptor, whereas, the $B_2$ receptor antagonist HOE 140 (Hock, F. J. et al. *British Journal of Pharmacology* 102, 769–773 (1991)) does not. Therefore, the expressed receptor has the pharmacological characteristics of the $B_1$ receptor subtype. The $B_1$ bradykinin receptor has been implicated in chronic inflammation and hyperalgesia, whereas the $B_2$ receptor appears to mediate acute inflammatory and algesic responses. The availability of the cloned human $B_1$ bradykinin receptor allows the identification of modulators useful in $B_1$-mediated diseases and conditions such as hyperalgesia, as well as acute and chronic inflammatory processes.

The present invention is also directed to methods for screening for compounds which modulate the expression of DNA or RNA encoding $B_1$ as well as the function of B1 protein in vivo. Compounds which modulate these activities may be DNA, RNA, peptides, proteins, or non-proteinaceous organic molecules. Compounds may modulate by increasing or attenuating the expression of DNA or RNA encoding $B_1$, or the function of $B_1$ protein. Compounds that modulate the expression of DNA or RNA encoding $B_1$ or the function of $B_1$ protein may be detected by a variety of assays. The assay may be a simple "yes/no" assay to determine whether there is a change in expression or function. The assay may be made quantitative by comparing the expression or function of a test sample with the levels of expression or function in a standard sample.

Kits containing B1 DNA, antibodies to $B_1$, or $B_1$ protein may be prepared. Such kits are used to detect DNA which hybridizes to $B_1$ DNA or to detect the presence of $B_1$ protein or peptide fragments in a sample. Such characterization is useful for a variety of purposes including but not limited to forensic analyses and epidemiological studies.

The DNA molecules, RNA molecules, recombinant protein and antibodies of the present invention may be used to screen and measure levels of $B_1$ DNA, $B_1$ RNA or $B_1$ protein. The recombinant proteins, DNA molecules, RNA molecules and antibodies lend themselves to the formulation of kits suitable for the detection and typing of $B_1$. Such a kit would comprise a compartmentalized carrier suitable to hold in close confinement at least one container. The carrier would further comprise reagents such as recombinant $B_1$ protein or anti-$B_1$ antibodies suitable for detecting $B_1$. The carrier may also contain a means for detection such as labeled antigen or enzyme substrates or the like.

Nucleotide sequences that are complementary to the $B_1$ encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other $B_1$ antisense oligonucleotide mimetics. $B_1$ antisense molecules may be introduced into cells by microinjection, liposome encapsulation or by expression from vectors harboring the antisense sequence. $B_1$ antisense therapy may be particularly useful for the treatment of diseases where it is beneficial to reduce $B_1$ activity.

$B_1$ gene therapy may be used to introduce $B_1$ into the cells of target organs. The $B_1$ gene can be ligated into viral vectors which mediate transfer of the $B_1$ DNA by infection of recipient host cells. Suitable viral vectors include retrovirus, adenovirus, adeno-associated virus, herpes virus, vaccinia virus, polio virus and the like. Alternatively, $B_1$ DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo $B_1$ gene therapy. $B_1$ gene therapy may be particularly useful for the treatment of diseases where it is beneficial to elevate $B_1$ activity.

Pharmaceutically useful compositions comprising $B_1$ DNA, $B_1$ RNA, or $B_1$ protein, or modulators of $B_1$ receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose $B_1$ related disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the $B_1$ receptor or its activity while minimizing any potential toxicity. In addition, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient for use in the modulation of $B_1$ receptors can be administered in a wide variety of therapeutic dosage forms in conventional vehicles for administration. For example, the compounds can be administered in such oral dosage forms as tablets, capsules (each including timed release and sustained release formulafions), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a $B_1$ modulating agent.

The daily dosage of the products may be varied over a wide range from 0.01 to 1,000 mg per adult human/per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the $B_1$ receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The following examples illustrate the present invention without, however, limiting the same thereto.

EXAMPLE 1

RNA Isolation

Oocyte Injections:

Injection of MRNA or cRNA into Xenopus oocytes was done by a modification of established protocols (A. Coleman, *Transcription and Translation: A Practical Approach*. B. D. Hanes, S. J. Higgins, Eds., 1984); Y. Masu, et al., *Nature* 329, 836–838 (1987)). Oocytes were surgically removed from either albino or pigmented 0.17% tricaine anesthetized *Xenopus laevis* (Xenopus One). The excised ovarian lobes were teased apart with jeweler's forceps and then placed into OR-2 (82.5 mM NaCl, 2 mM KCl, 1 mM $MgCl_2$, 5 mM HEPES pH 7.4) containing 2 mg/ml collagenase B (Boehringer Mannhiem) for 2 hours at room temperature with a change of the buffer at 1 hour. Isolated oocytes were repeatedly washed in OR-2 until the supernatant remained clear. Stage 5 and 6 oocytes were selected and cultured overnight in supplemented OR-2 (OR-2 containing 1.8 mM $CaCl_2$, 0.5 mg/ml gentamycin and 0.5 mM theophylline). Initially, oocytes were injected with 46 nl of RNA at a concentration of 1 or 2 mg/ml in $H_2O$, once the pool size became less than 30 clones the cRNA concentration was decreased to 40 ng/ml. RNA was injected using a Nanoject automatic oocyte injector (Drummond Scientific) and injection needles were pulled from 3.5" Drummond capillaries using a Flaming/Brown Micropipette puller (Sutter Instruments). Two to three days after the RNA injection, oocytes were injected with 92 ng of aequorin (Friday Harbor Photoproteins) resuspended in 46 nl of 1 mM EDTA, as previously described (K. Sandberg, A. J. Markwick, D. P. Trinh, K. J. Catt, *FEBS Letters* 241, 177–180 (1988); E. Giladi, E. R. Spindel, *BioTechniques* 10, 744–747 (1991)). The following day, individual oocytes placed in wells of a microtiter dish containing 225 $\mu$l OR-2 were challenged with peptide agonists and the aequorin photo response was measured using a ML3000 Microtiter plate luminometer (Dynatech). Oocytes were challenged with several peptides (Peninsula Laboratories) as described in the text and figure legends.

Injection of poly(A)$^+$ MRNA prepared from IL-1β induced IMR-90 cells into *Xenopus laevis* oocytes resulted in aequorin mediated luminescence in response to either the $B_1$ agonist des-Arg$^{10}$kallidin or the $B_2$ agonist BK (FIG. 3). The poly(A)$^+$ MRNA was size-fractionated over a sucrose gradient, fractions were injected into oocytes, and the oocytes were assayed for their ability to respond to either BK or des-Arg$^{10}$kallidin. The $B_1$ and $B_2$ receptor transcripts were clearly separated by the size fractionation. The mRNA mediating the response to des-Arg$^{10}$kallidin exhibited an apparent size of 1.6–1.8 kb, whereas, the mRNA mediating the response to BK had an apparent size of 4.4–4.6 kb. The apparent size of the MRNA encoding bradykinin response is consistent with the previously determined size of the $B_2$ bradykinin receptor transcript (A. E. McEachem, et al., *Proc. Natl. Acad. Sci.* 88, 7724–7728 (1991); J. F. Hess, et al., *Molecular Pharmacology* 45, 1–8 (11994)).

EXAMPLE 2

RNA Fractionation

IMR-90 cells (ATCC CCL 186) were grown in MEM supplemented with 10% fetal calf serum, glutamine, nonessential amino acids, sodium pyruvate, penicillin and streptomycin (Gibco). Two and a half hours prior to mRNA extraction, IMR-90 cells were exposed to 200 pg/ml IL-1β (R & D Systems). mRNA was purified from these cells using the PolyAtract mRNA isolation system (Promega) and resuspended in $H_2O$ at a concentration of 2 mg/ml.

IMR-90 mRNA was size fractionated on a continuous 6 to 20% sucrose gradient in 15 mM PIPES (pH 6.5), 5 mM EDTA and 0.25% N-lauroylsarcosine. 480 μg of mRNA from the IL-1β induced IMR-90 cells was heated to 65° C. for 3 minutes, quickly cooled on ice, and loaded onto the gradient. The RNA was size fractionated by centrifugation at 18° C. for 19 hours at 77,000xg. Fractions (450R) from each gradient were collected from the bottom of the tube and their absorbance at OD 260 monitored. Fractions were ethanol precipitated twice and resuspended to a final concentration of 1 μg/μl. RNA sizes determination was based on the migration pattern of 80 μg of 9.49–0.24 Kb RNA markers (BRL) loaded on a parallel gradient.

Library Construction:

A peak RNA fraction from the sucrose gradient which gave a response to des-$Arg^{10}$kallidin was utilized to generate a cDNA library. The library was constructed in the mammalian expression vector pcDNA3 using a combination of random hexamers and oligo dT to prime the first strand cDNA synthesis. First strand cDNA synthesis of approximately 3 μg of fraction 14 size-selected mRNA was primed with 50 ng random hexamers and 400 ng of a Not I oligo dT oligonucleotide and synthesized with the BRL Superscript II reverse transcriptase (Gibco-BRL). Following second strand synthesis Bst XI/Eco RI adaptors (Invitrogen) were ligated onto the ends and the cDNA was passed over a BRL cDNA sizing column (Gibco-BRL). The cDNA was cloned into the Bst XI site of pcDNA3 (Invitrogen, San Diego, Calif.) containing a modified polylinker. Plasmid DNA was transformed into XL-1 Blue cells (Stratagene). The library contained greater than 90% inserts with an average insert size of 1.9 kb.

The library was plated in pools of approximately 5000 clones that were used to synthesize cRNA using the T7 RNA polymerase. Colonies were plated on Colony/Plaque screen filters (NEN/Dupont) that were placed on Luria-Bertani (LB) agar plates supplemented with 100 ug/ml ampicillin (Sigma). Replica filters were made, the bacterial colonies were scraped in LB broth, and a frozen glycerol stock was prepared. Plasmid DNA was made using the Wizard DNA purification system (Promega). Plasmid DNA was linearized with Not I and cRNA was synthesized using T7 RNA polymerase with the mCAP RNA capping kit (Stratagene).

Figure 4A:
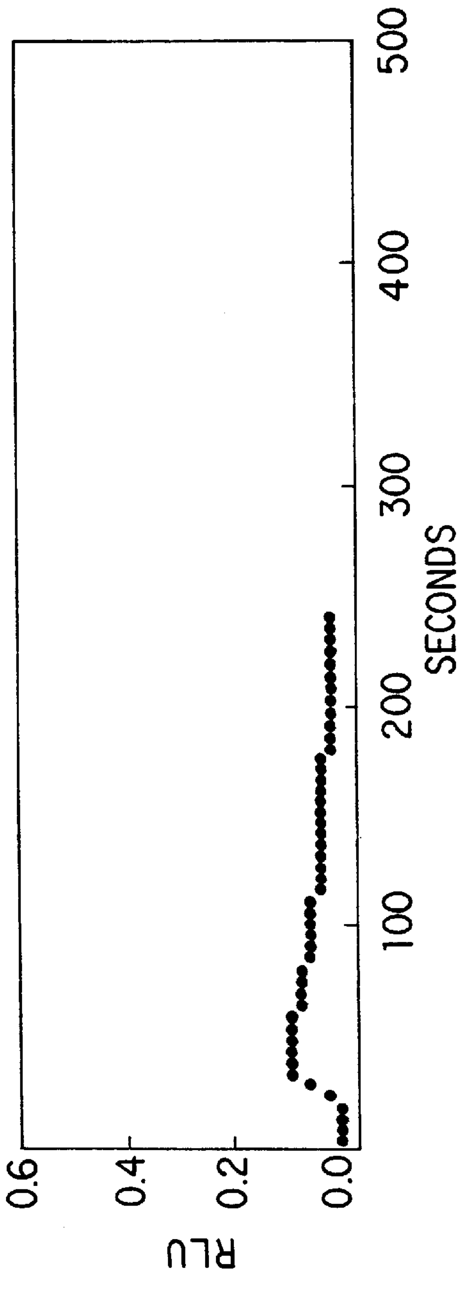
FIG. 4 panels A and B—Luminometer tracings of individual oocytes in response to 20 nM des-$Arg^{10}$kallidin are shown. Panel A shows the signal obtained using total poly $(A)^+$ mRNA isolated from IL-1β induced IMR-90 cells. Panel B shows the signal obtained using clone 33E9 cRNA.
Figure 4B:
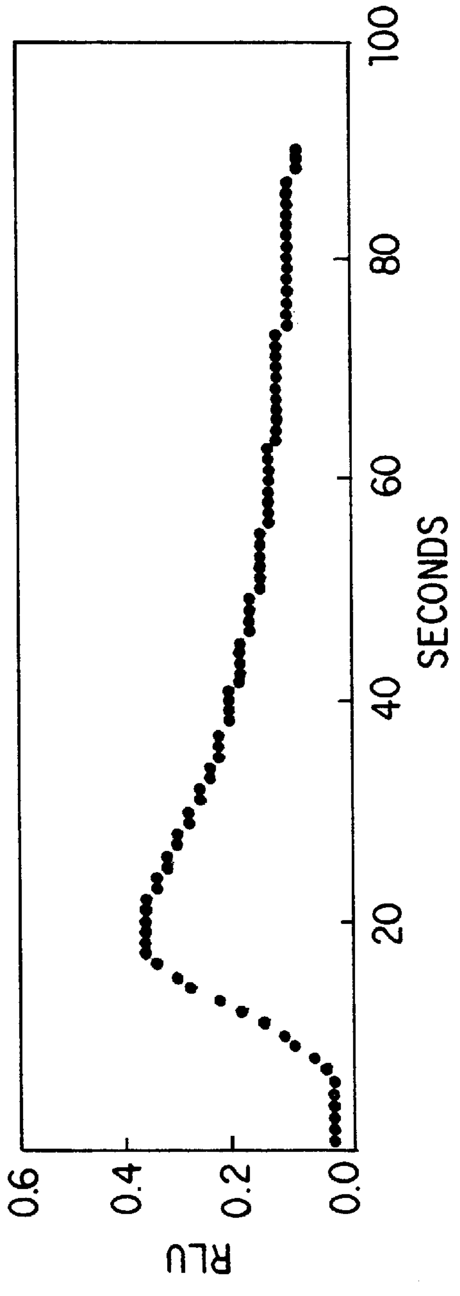

Of the twenty-five pools of cRNA that were injected into Xenopus oocytes, 11 exhibited aequorin-mediated luminescence in response to des-$Arg^{10}$kallidin. The pool that gave the most robust response was replated and fractionated into 25 pools of approximately 800 clones. Eight pools exhibited a response to des-$Arg^{10}$kallidin. The strongest positive pool was further examined using electrophysiology to monitor the $Ca^{2+}$ sensitive $Cl^-$ channel. Des-$Arg^{10}$kallidin produced a response that was blocked by the $B_1$ receptor antagonist des-$Arg^{10}$[Leu]$^9$kallidin. This pool was then subdivided into 32 pools of approximately 25 individual clones. Two positive pools, containing 14 and 34 clones, were identified. cRNA was prepared from individual clones and analyzed in Xenopus oocytes. Three individual clones were found to elicit a des-$Arg^{10}$kallidin response (FIGS. 4 A&B). Restriction analysis, Southern blotting, and preliminary DNA sequence analysis indicated that these individual clones were similar. One clone, 33E9, was chosen for further DNA sequence analysis, expression, and pharmacological characterization. The DNA sequence of both strands was determined by either manual sequencing using Sequenase (USB) or automated sequencing using an ABI 373A sequencing unit (Perkin Elmer).

Primary Structure Of The $B_1$ Receptor

The DNA sequence of the approximately 1307 bp clone 33E9 contains an open reading frame of about 1059 bp (FIGS. 1 and 2). The proposed initiator methionine at nucleotide about 209 conforms to the Kozak sequence (M. Kozak, *Journal of Cell Biology* 108, 229–241 (1989)) at the +4 position but not at the −3 position. The approximately 208 nucleotide putative 5' untranslated sequence contains a region of relatively high nucleotide identity to a wide variety of human DNA sequences, suggestive of a human repetitive element. The apparent repetitive element appears to be an authentic portion of the mRNA transcript since it was detected in several independently derived cDNA clones. The DNA sequence identity between the open reading frame in clone 33E9 and the DNA encoding the human $B_2$ receptor (S. J. Powell, et al., *Genomics* 15, 435–438 (1993); J. F. Hess, J. A. Borkowski, G. S. Young, C. D. Strader, R. W. Ransom, *Biochem. and Biophys. Res. Comm.* 184, 260–268 (1992); D. Eggerickx, E. Raspe, D. Bertrand, G. Vassart, M. Parmentier, *Biochem. Biophys. Res. Comm.* 187, 1306–1313 (1992)) is 54%. This is consistent with the inability of genomic Southern analyses to detect this gene (A. E. McEachern, et al., *Proc. Natl. Acad. Sci.* 88, 7724–7728 (1991); J. F. Hess, et al., *Molecular Pharmacology* 45, 1–8 (1994)).

The proposed amino acid sequence encoded by the open reading frame is 36% identical to the $B_2$ bradykinin receptor. A hydrophobicity plot of the amino acid sequence reveals the seven potential transmembrane spanning domains that are characteristic of G-protein coupled receptors (H. G. Dohlman, J. Thomer, M. G. Caron, R. J. Lefkowitz, *Ann. Rev. Biochem.* 60, 653–688 (1991); C. D. Strader, I. S. Sigal, R. A. F. Dixon, *FASEB* 3, 1825–1832 (1989)). Two conserved Cys residues that are proposed to form a disulfide bond between the first and second extracellular loops in nearly all G-protein coupled receptors are also present in the sequence. There are two potential N-linked glycosylation sites in the N-terminal domain of the sequence and one putative site for N-linked glycosylation in the second extracellular loop region. Potential protein kinase C phosphorylation sites are present in intracellular domain 2 and the carboxy-terminal tail. Similar potential phosphorylation sites in other G-protein coupled receptors have been implicated in short-term desensitization of the receptor following agonist stimulation.

EXAMPLE 3

Genomic DNA Cloning of the $B_1$ Receptor

A human genomic DNA library is constructed in the cosmid sCOS vector using genomic DNA isolated from human foreskin fibroblast HSF42 cells (Chartrain, N.A., et al. *Journal of Biological Chemistry* 269, 6765–6772 (1994)). The recombinant DNA library constructed from genomic DNA of human cells is plated on Colony/Plaque screen hybridization transfer membrane (Dupont/NEN) at a density of approximately 30,000 colonies per plate. Replicas of master plates are lysed and processed for hybridization using standard protocols (Sambrook, J., Fritsch, E. F., Maniatis, T. in Molecular Cloning: A Laboratory Manual, Second Edition, Cold Spring Harbor Laboratory, Cold Spring Harbor, N.Y., 1989). The DNA is UV crosslinked to the membrane with a Stratalinker (Stratagene). The filters are incubated overnight at 42° C. with radiolabeled probe in 50% formamide hybridization solution, [5×SSC, 5×Denhardt's, 100 μg/ml DNA (Sigma)]. The probe, a DNA fragment containing the coding sequence of the human $B_1$ bradykinin receptor, is generated by random prime labeling (Boehringer Mannheim Biochemicals) in the presence of [α-$^{32}$P]dCTP (3000 Ci/mmole). Filters are washed at a final stringency of 0.1×SSC, 0.1% SDS at 42° C. Positives are rescreened to isolate single colonies. DNA is prepared from positive colonies, digested with restriction enzymes, and Southern blot analysis is done to identify restriction fragments for subcloning. A fragment is subcloned into pSP72 (Promega).

EXAMPLE 4

Cloning of B1 cDNA into a Mammalian Expression Vector Mammalian Cell Expression and Characterization Transient expression of the cloned $B_1$ bradykinin receptor in COS-7 cells was accomplished by electroporation using a Biorad Gene Pulser. Three days post-transfection, cells were processed for a whole cell binding assay as previously published (K. A. Schneck, J. F. Hess, G. Y. Stonesifer, R. W. Ransom, *European Journal of Pharmacology-Molecular Pharmacology Section* 266, 277–282 (1994)) or membranes were prepared as described previously (Huang, R.-R. C., Dehaven, R. N., Cheung, A. H., Diehl, R. E., Dixon, R. A. F., Strader, C.D., *Molecular Pharmacology* 37, 304–310 (1990)) and radioligand binding measured as follows. Displacement studies were done with 1 nM [des-Arg$^{10}$],[3,4-$^3$H(N)]-kallidin (NEN) in the presence of varying concentrations of competitor compounds. Binding assays were performed at room temperature for 45 minutes. Reactions were terminated by filtration using an Inotech cell harvester onto glass fiber filters (Inotech) that had been briefly soaked in 0.3% polyethyleneimine. The filters were washed five times with 1 ml per well of cold PBS and counted in a liquid scintillation counter. Alternatively, reactions were collected using a Tomtec cell harvester 96 onto 0.3% polyethyleneimine presoaked glass fiber filters (Pharmacia, printed filtermat for use with the 1205 Betaplate). The filter was washed five times with a total of 10 ml per well of cold 1×PBS, dried and sealed in a bag (Pharmacia) containing scintillation fluid. Counting was accomplished using a $LKB_{1205}$ Betaplate liquid scintillation counter.

The $B_1$ bradykinin receptor clone 33E9 was transfected into COS-7 cells and the pharmacological properties of the expressed receptor were determined. Scatchard analysis of saturation binding data with [$^3$H]des-Arg$^{10}$kallidin indicated a $K_d$ of about 1.0 nM and a $B_{max}$ of approximately 120 fmol/mg protein. Mock transfected COS-7 cells do not contain any specific binding for [$^3$H]des-Arg$^{10}$kallidin.

Figure 5:
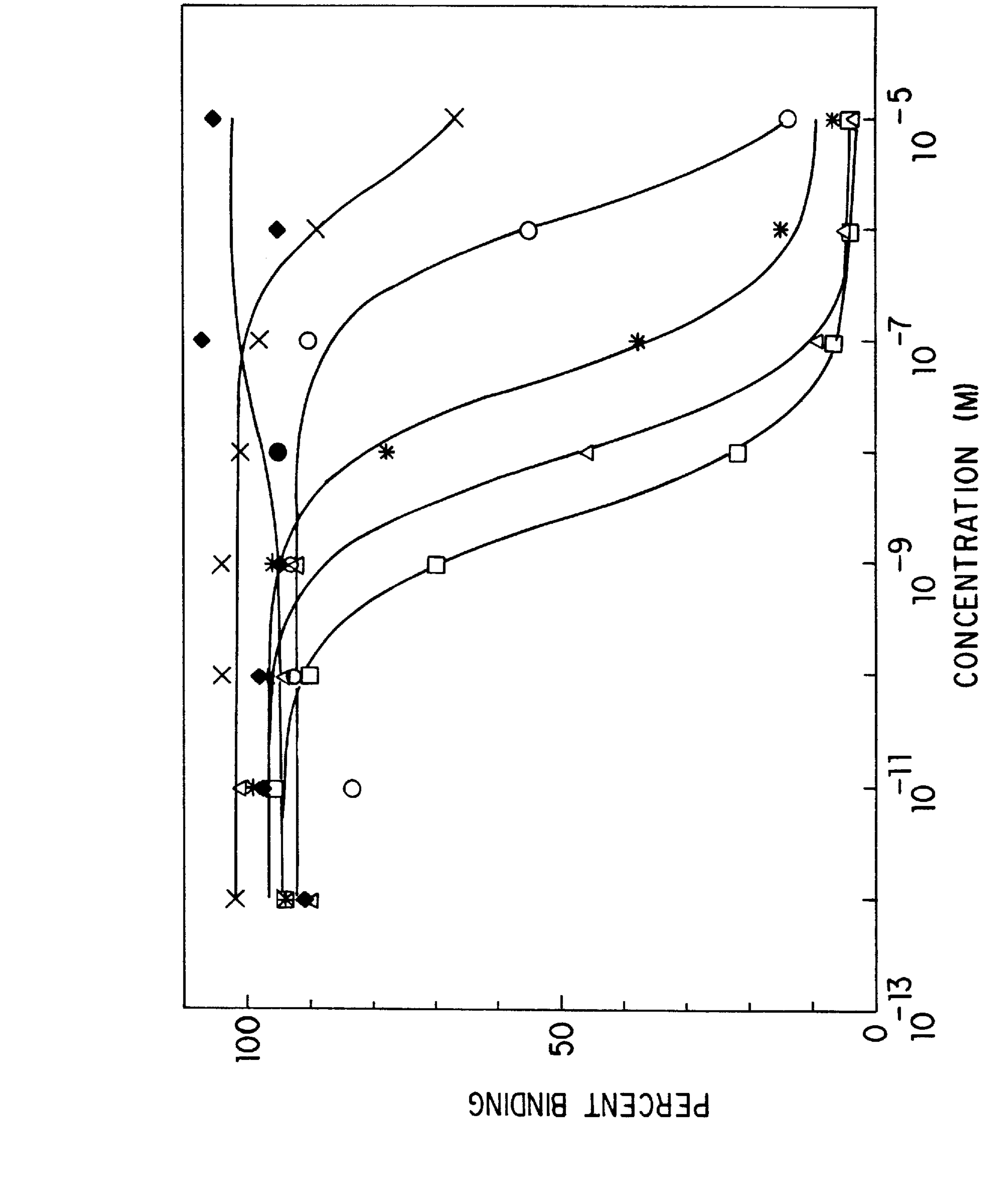
FIG. 5—Displacements of 1 nM [$^3$H]des-$Arg^{10}$kallidin from COS-7 cells expressing the human $B_1$ bradykinin receptor by increasing concentrations of compounds are shown. Symbols for compounds: des-$Arg^{10}$kallidin (q), des-$Arg^{10}$[$Leu^9$]kallidin (Δ), kallidin (*), HOE 140 (u), des-$Arg^9$bradykinin (O), and bradykinin (X).

The ability of several bradykinin receptor agonists and antagonists to displace 1 nM [$^3$H]des-Arg$^{10}$kallidin from the cloned receptor was assessed (FIG. 5, Table 1). The $IC_{50}$ for displacement of 1 nM [$^3$H]des-Arg$^{10}$kallidin by bradykinin from the cloned receptor is >10 μM. The low affinity of this receptor for bradykinin and high affinity for des-Arg$^{10}$kallidin argues strongly that this cloned bradykinin receptor is of the $B_1$ subtype. Competition binding studies yielded a rank order of affinity for kinin agonists of des-Arg$^{10}$kallidin>kallidin>des-Arg$^9$bradykinin>>bradykinin at the cloned human receptor. This is very similar to the rank order of potency reported for the rabbit $B_1$ bradykinin receptor and identical to that observed for the $B_1$ receptor in IMR-90 cells (Table 1). Both the cloned human receptor and the $B_1$ receptor in IMR-90 cells exhibit a relatively low affinity for the "classical" $B_1$ receptor agonist des-Arg$^9$bradykinin which has been reported to a have a high affinity for the $B_1$ receptor in rabbit aorta (K. A. Schneck, J. F. Hess, G. Y. Stonesifer, R. W. Ransom, *European Journal of Pharmacology-Molecular Pharmacology Section* 266, 277–282 (1994); D. Regoli, J. Barabe, *Pharmacological Reviews* 32, 1–46 (1980)). The $B_1$ bradykinin receptor present in human aorta also has a relatively low affinity for des-Arg$^9$bradykinin (>1000 nM, R. W. R, unpublished data). These results taken together with the lower affinity for des-Arg$^9$bradykinin relative to des-Arg$^{10}$kallidin in the rabbit (K. A. Schneck, J. F. Hess, G. Y. Stonesifer, R. W. Ransom, *European Journal of Pharmacology-Molecular Pharmacology Section* 266, 277–282 (1994); D. Regoli, J. Barabe, *Pharmacological Reviews* 32, 1–46 (1980)) suggest that the most potent natural ligand for the $B_1$ receptor is des-Arg$^{10}$kallidin . Therefore, the $B_1$ receptor cloned here appears to be the human homologue of the $B_1$ receptor present in rabbit aorta, and the lower affinity of the human receptor for des-Arg$^9$bradykinin appears to be a consequence of species differences.

TABLE 1

Comparison of the peptide binding properties of the cloned human $B_1$ bradykinin receptor in transiently transfected COS-7 cells (COS 33E9) with the $B_1$ receptor in IMR-99 cells (IMR-90).
The $IC_{50}$'s were determined by the displacement of 1 nM [$^3$H] des-Arg$^{10}$kallidin in the membrane binding assay described above.

| Competitor | COS 33E9 | IMR-90 |
|---|---|---|
| des-Arg$^{10}$kallidin | 2.6 nM | 2.3 nM |
| des-Arg$^{10}$Leu$^9$kallidin | 9 nM | 7.8 nM |
| Kallidin | 46 nM | 44 nM |
| Hoe 140 | >10 μM | >10 μM |
| Bradykinin | >10 μM | >10 μM |
| des-Arg$^9$bradykinin | 1500 nM | 660 nM |
| des-Arg$^9$Leu$^8$bradykinin | 605 nM | 266 nM |
| des-Arg$^{10}$HOE 140 | 94 nM | 40 nM |
| Met-Lys-Bradykinin | 71 nM | 40 nM |
| Substance P | >10 μM | >10 μM |
| $Bradykinin_{(2-9)}$ | >10 μM | >10 μM |
| $Bradykinin_{(1-7)}$ | >10 μM | >10 μM |
| Neurotensin | >10 μM | >10 μM |
| Leu-Enkephalin | >10 μM | >10 μM |
| Angiotensin II | >10 μM | >10 μM |
| Acetylated $Neurotensin_{(8-13)}$ | >10 μM | >10 μM |
| Arg Vasopressin | >10 μM | >10 μM |
| Oxytocin | >10 μM | >10 μM |
| $Dynorphin_{(1-17)}$ | >7 μM | >7 μM |
| Endothelin I | >1 μM | >1 μM |

The ability of several bradykinin receptor antagonists to displace 1 nM [$^3$H]des-Arg$^{10}$kallidin was also analyzed. The cloned receptor has high affinity binding for the $B_1$ specific antagonist des-Arg$^{10}$[Leu$^9$]kallidin and des-Arg$^9$[Leu$^8$] bradykinin (FIG. 5, Table 1). The potent $B_2$ specific antagonist HOE 140 has a very low affinity for the cloned receptor. However, the removal of the C-terminal Arg from HOE 140 results in a significant increase in affinity, as expected for a $B_1$ receptor (K. Wirth, et al., *European Journal of Pharmacology* 205, 217–218 (1991)). Therefore, the interaction of the cloned receptor with bradykinin receptor antagonists is consistent with the $B_1$ receptor classification.

In summary, we have utilized an expression cloning strategy to isolate a clone encoding a human $B_1$ bradykinin receptor. This receptor was isolated by its ability, when expressed in Xenopus oocytes, to functionally respond to the $B_1$ receptor agonist des-Arg$^{10}$kallidin. The cloned receptor is a G-protein coupled receptor that is most similar in amino acid sequence to the $B_2$ bradykinin receptor. The pharmacological properties of the cloned receptor expressed in mammalian cells are characteristic of the $B_1$ bradykinin receptor classification.

EXAMPLE 5

Cloning of the B1 cDNA into *E. coli* Expression Vectors

Recombinant $B_1$ is produced in *E. coli* following the transfer of the $B_1$ expression cassette into *E. coli* expression vectors, including but not limited to, the pET series (Novagen). The pET vectors place $B_1$ expression under control of the tightly regulated bacteriophage T7 promoter. Following transfer of this construct into an *E. Coli* host which contains a chromosomal copy of the T7 RNA polymerase gene driven by the inducible lac promoter, expression of $B_1$ is induced when an appropriate lac substrate (IPTG) is added to the culture. The levels of expressed $B_1$ are determined by the assays described herein.

The cDNA encoding the entire open reading frame for $B_1$ is inserted into the NdeI site of pET 11a. Constructs in the positive orientation are identified by sequence analysis and used to transform the expression host strain BL21. Transformants are then used to inoculate cultures for the production of $B_1$ protein. Cultures may be grown in M9 or ZB media, whose formulation is known to those skilled in the art. After growth to an $OD_{600}$=1.5, expression of $B_1$ is induced with 1 mM IPTG for 3 hours at 37° C.

EXAMPLE 6

Cloning of B1 cDNA into a Vectors for Expression in Insect Cells

Baculovirus vectors, which are derived from the genome of the AcNPV virus, are designed to provide high level expression of cDNA in the Sf9 line of insect cells (ATCC CRL #1711). Recombinant baculoviruses expressing $B_1$ cDNA is produced by the following standard methods (InVitrogen Maxbac Manual): the $B_1$ cDNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, P. A., *Nuc. Acid. Res.* 18, 5667 (1990)] into Sf9 cells. Recombinant pAC360 viruses are identified by the absence of inclusion bodies in infected cells and recombinant pBlueBac viruses are identified on the basis of β-galactosidase expression (Summers, M. D. and Smith, G. E., Texas Agriculture Exp. Station Bulletin No. 1555). Following plaque purification, $B_1$ expression is measured by the assays described herein.

The cDNA encoding the entire open reading frame for $B_1$ is inserted into the BamHI site of pBlueBacII. Constructs in the positive orientation are identified by sequence analysis and used to transfect Sf9 cells in the presence of linear AcNPV wild type DNA.

Authentic, active $B_1$ is found in association with the infected cells. Active $B_1$ is extracted from infected cells by hypotonic or detergent lysis.

Alternatively, the human $B_1$ receptor is expressed in the Drosophila Schneider 2 cell line by cotransfection of the Schneider 2 cells with a vector containing the $B_1$ receptor DNA downstream and under control of an inducible metallothionin promoter, and a vector encoding the G418 resistant neomycin gene. Following growth in the presence of G418, resistant cells are obtained and induced to express $B_1$ receptor by the addition of CuSO4. Identification of modulators of the $B_1$ receptor is accomplished by assays using either whole cells or membrane preparations.

EXAMPLE 7

Cloning of B1 cDNA into a Yeast Expression Vector

Recombinant $B_1$ is produced in the yeast *S. cerevisiae* following the insertion of the optimal $B_1$ cDNA cistron into expression vectors designed to direct the intracellular or extracellular expression of heterologous proteins. In the case of intracellular expression, vectors such as EmBLyex4 or the like are ligated to the $B_1$ cistron [Rinas, U. et al., *Biotechnology* 8, 543–545 (1990); Horowitz B. et al., *J. Biol. Chem.* 265, 4189–4192 (1989)]. For extracellular expression, the $B_1$ cistron is ligated into yeast expression vectors which fuse a secretion signal. The levels of expressed $B_1$ are determined by the assays described herein.

EXAMPLE 8

Purification of Recombinant B1

Recombinantly produced $B_1$ may be purified by antibody affinity chromatography.

$B_1$ antibody affinity columns are made by adding the anti-$B_1$ antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized $B_1$ or $B_1$ subunits are slowly passed through the column. The column is then washed with phosphate- buffered saline together with detergents until the optical density (A280) falls to background, then the protein is eluted with 0.23 M glycine-HCl (pH 2.6) together with detergents. The purified $B_1$ protein is then dialyzed against phosphate buffered saline.

What is claimed is:

1. A monospecific antibody immunologically reactive with a bradykinin $B_1$ receptor, the bradykinin $B_1$ receptor comprising the amino acid sequence as set forth in SEQ ID NO:2, or portion thereof.

2. The antibody of claim 1, wherein the antibody blocks activity of the bradykinin $B_1$ receptor.

3. A monospecific antibody immunologically reactive with a bradykinin $B_1$ receptor, the bradykinin $B_1$ receptor consisting of the amino acid sequence as set forth in SEQ ID NO:2, or portion thereof.

4. The antibody of claim 3, wherein the antibody blocks activity of the bradykinin $B_1$ receptor.

5. A polyclonal antibody preparation which is immunologically reactive with a bradykinin $B_1$ receptor, the bradykinin $B_1$ receptor comprising the amino acid sequence as set forth in SEQ ID NO:2, or portion thereof.

6. The polyclonal antibody preparation of claim 5, wherein the antibody preparation blocks activity of the bradykinin $B_1$ receptor.

7. A polyclonal antibody preparation which is immunologically reactive with a bradykinin $B_1$ receptor, the bradykinin $B_1$ receptor consists of the amino acid sequence as set forth in SEQ ID NO:2, or portion thereof.

8. The polyclonal antibody preparation of claim 7, wherein the antibody preparation blocks activity of the bradykinin $B_1$ receptor.

* * * * *